US012758268B2

(12) United States Patent

Gladieux et al.

(10) Patent No.: US 12,758,268 B2
(45) Date of Patent: Oct. 13, 2026

(54) POLYAXIAL SCREW ASSEMBLY

(71) Applicant: SeaSpine Orthopedics Corporation, Carlsbad, CA (US)

(72) Inventors: Corey Noel Gladieux, Carlsbad, CA (US); Leah Beyer Sherman, Carlsbad, CA (US)

(73) Assignee: SeaSpine Orthopedics Corporation, Carlsbad, CA (US)

(*) Notice: Subject to any disclaimer, the term of this patent is extended or adjusted under 35 U.S.C. 154(b) by 97 days.

(21) Appl. No.: 18/813,713

(22) Filed: Aug. 23, 2024

(65) Prior Publication Data

US 2025/0064487 A1 Feb. 27, 2025

Related U.S. Application Data

(60) Provisional application No. 63/578,766, filed on Aug. 25, 2023.

(51) Int. Cl.

*A61B 17/70* (2006.01)
*A61B 17/86* (2006.01)

(52) U.S. Cl.

CPC ...... *A61B 17/7035* (2013.01); *A61B 17/7032* (2013.01); *A61B 17/8605* (2013.01)

(58) Field of Classification Search

CPC ........................ A61B 17/7035; A61B 17/7037
See application file for complete search history.

(56) References Cited

U.S. PATENT DOCUMENTS

| | | | |
|---|---|---|---|
| 5,733,285 | A | 3/1998 | Errico et al. |
| 6,187,005 | B1 | 2/2001 | Brace et al. |
| 6,733,502 | B2 | 5/2004 | Altarac et al. |
| 7,090,674 | B2 | 8/2006 | Doubler et al. |
| 7,186,255 | B2 | 3/2007 | Baynham |
| 7,264,621 | B2 | 9/2007 | Coates et al. |
| 7,291,151 | B2 | 11/2007 | Alvarez |
| 7,445,627 | B2 | 11/2008 | Hawkes et al. |
| 7,476,239 | B2 | 1/2009 | Jackson |
| 7,559,943 | B2 | 7/2009 | Mujwid |
| 7,625,394 | B2 | 12/2009 | Molz, IV et al. |
| 7,686,835 | B2 | 3/2010 | Warnick |
| 7,699,876 | B2 | 4/2010 | Barry et al. |
| 7,789,900 | B2 | 9/2010 | Levy et al. |
| 7,828,829 | B2 | 11/2010 | Ensign |
| 7,901,437 | B2 | 3/2011 | Jackson |

(Continued)

FOREIGN PATENT DOCUMENTS

| | | | |
|---|---|---|---|
| EP | 1210914 | B1 | 5/2005 |
| EP | 2146655 | A1 | 1/2010 |

(Continued)

*Primary Examiner* — Andrew Yang
(74) *Attorney, Agent, or Firm* — Dinsmore & Shohl LLP

(57) ABSTRACT

A polyaxial bone screw system and method for connecting a longitudinal rod to multiple bones or bone portions. The system may include a bone fastener having a shank and a shank head; a polyaxial body to receive the shank head; and a collet for applying force to exterior surface of the shank head when the collet is acted upon by a rod, which is pressed onto the collet via a set screw received in the polyaxial body. The force applied to the shank head by the collet is adequate to temporarily lock the desired orientation of the shank with respect to the polyaxial body.

18 Claims, 8 Drawing Sheets

(56) References Cited

U.S. PATENT DOCUMENTS

| | | | | |
|---|---|---|---|---|
| 7,922,748 | B2 | 4/2011 | Hoffman | |
| 7,935,135 | B2 | 5/2011 | Mujwid | |
| 7,967,850 | B2 | 6/2011 | Jackson | |
| 8,002,806 | B2 | 8/2011 | Justis | |
| 8,012,188 | B2 | 9/2011 | Melkent et al. | |
| 8,016,862 | B2 | 9/2011 | Felix et al. | |
| 8,075,590 | B2 | 12/2011 | Janowski et al. | |
| 8,075,600 | B2 | 12/2011 | Schlaepfer | |
| 8,080,036 | B2 | 12/2011 | Shim et al. | |
| 8,083,776 | B2 | 12/2011 | Alvarez | |
| 8,100,947 | B2 | 1/2012 | Ensign et al. | |
| 8,142,481 | B2 | 3/2012 | Warnick | |
| 8,197,517 | B1 | 6/2012 | Lab et al. | |
| 8,257,396 | B2 | 9/2012 | Jackson | |
| 8,267,980 | B2 | 9/2012 | Felix | |
| 8,328,817 | B2 | 12/2012 | Strauss | |
| 8,361,129 | B2 | 1/2013 | Chao | |
| 8,366,747 | B2 | 2/2013 | Shluzas | |
| 8,366,753 | B2 | 2/2013 | Jackson | |
| 8,377,101 | B2 | 2/2013 | Barrus et al. | |
| 8,465,530 | B2 | 6/2013 | Hammill, Sr. et al. | |
| 8,556,938 | B2 | 10/2013 | Jackson et al. | |
| 8,603,145 | B2 | 12/2013 | Forton et al. | |
| 8,608,780 | B2 | 12/2013 | Forton et al. | |
| 8,636,769 | B2 | 1/2014 | Jackson | |
| 8,636,777 | B2 | 1/2014 | Jackson | |
| 8,636,778 | B2 | 1/2014 | Gephart et al. | |
| 8,657,858 | B2 | 2/2014 | Garamszegi et al. | |
| 8,696,717 | B2 | 4/2014 | Rock et al. | |
| 8,814,919 | B2 | 8/2014 | Barrus et al. | |
| 8,840,652 | B2 | 9/2014 | Jackson | |
| 8,845,693 | B2 | 9/2014 | Smith et al. | |
| 8,876,869 | B1 | 11/2014 | Schafer et al. | |
| 8,915,945 | B2 | 12/2014 | Carson et al. | |
| 8,951,294 | B2 | 2/2015 | Gennari et al. | |
| 8,979,904 | B2 | 3/2015 | Jackson et al. | |
| 8,998,967 | B2 | 4/2015 | Biedermann et al. | |
| 9,005,259 | B2 | 4/2015 | Biedermann et al. | |
| 9,034,021 | B2 | 5/2015 | Matthis et al. | |
| 9,060,811 | B2 | 6/2015 | Werner et al. | |
| 9,066,759 | B2 | 6/2015 | Biedermann et al. | |
| 9,101,404 | B2 | 8/2015 | Jackson | |
| 9,144,444 | B2 | 9/2015 | Jackson | |
| 9,168,069 | B2 | 10/2015 | Jackson et al. | |
| 9,173,684 | B2 | 11/2015 | Biedermann et al. | |
| 9,186,191 | B2 | 11/2015 | Berrevoets et al. | |
| 9,204,898 | B2 | 12/2015 | Gephart | |
| 9,289,246 | B2 | 3/2016 | Biedermann et al. | |
| 9,345,516 | B2 | 5/2016 | Biedermann et al. | |
| 9,351,766 | B2 | 5/2016 | Biedermann et al. | |
| 9,393,047 | B2 | 7/2016 | Jackson et al. | |
| 9,414,860 | B2 | 8/2016 | Boachie-Adjei et al. | |
| 9,414,863 | B2 | 8/2016 | Jackson | |
| 9,439,683 | B2 | 9/2016 | Jackson | |
| 9,452,006 | B2 | 9/2016 | Biedermann et al. | |
| 9,453,526 | B2 | 9/2016 | Black et al. | |
| 9,456,859 | B2 | 10/2016 | Peukert | |
| 9,480,517 | B2 | 11/2016 | Jackson et al. | |
| 9,486,246 | B2 | 11/2016 | Biedermann et al. | |
| 9,517,089 | B1 | 12/2016 | Casey et al. | |
| 9,522,021 | B2 | 12/2016 | Jackson et al. | |
| 9,526,529 | B2 | 12/2016 | Charvet | |
| 9,532,809 | B2 | 1/2017 | Biedermann et al. | |
| 9,603,629 | B2 | 3/2017 | Richelsoph | |
| 9,603,632 | B1 | 3/2017 | Gunn et al. | |
| 9,615,858 | B2 | 4/2017 | Doubler et al. | |
| 9,622,788 | B2 | 4/2017 | Rezach et al. | |
| 9,629,662 | B2 | 4/2017 | Arnold et al. | |
| 9,655,650 | B2 | 5/2017 | Blain et al. | |
| 9,655,656 | B2 | 5/2017 | Whipple | |
| RE46,431 | E | 6/2017 | Jackson | |
| 9,707,013 | B2 | 7/2017 | Rezach et al. | |
| 9,717,534 | B2 | 8/2017 | Jackson et al. | |
| 9,737,338 | B2 | 8/2017 | Bazille | |
| 9,750,540 | B2 | 9/2017 | Jackson | |
| 9,820,780 | B2 | 11/2017 | Duncan et al. | |
| 9,833,264 | B2 | 12/2017 | Jackson et al. | |
| 9,883,892 | B2 | 2/2018 | Jackson et al. | |
| 9,895,171 | B2 | 2/2018 | Webb | |
| 9,936,979 | B2 | 4/2018 | Peterson et al. | |
| 9,956,002 | B2 | 5/2018 | Jackson | |
| 9,956,006 | B2 | 5/2018 | Jackson | |
| 9,956,010 | B2 | 5/2018 | Richelsoph et al. | |
| 9,962,191 | B2 | 5/2018 | Barrus | |
| 9,962,196 | B2 | 5/2018 | McLean et al. | |
| 9,974,569 | B2 | 5/2018 | Lehmann, Jr. et al. | |
| 10,039,572 | B2 | 8/2018 | Harris et al. | |
| 10,064,657 | B2 | 9/2018 | Spitler | |
| 10,070,895 | B2 | 9/2018 | Barra et al. | |
| 10,076,361 | B2 | 9/2018 | Jackson | |
| 10,080,590 | B2 | 9/2018 | Abdou | |
| 10,111,694 | B2 | 10/2018 | Savage | |
| 10,219,838 | B2 | 3/2019 | Courtney et al. | |
| 10,231,757 | B2 | 3/2019 | Jackson | |
| 10,238,431 | B2 | 3/2019 | Jackson et al. | |
| 10,245,077 | B2 | 4/2019 | Jackson | |
| 10,258,385 | B1 | 4/2019 | Doubler et al. | |
| 10,278,740 | B2 | 5/2019 | Jackson | |
| 10,299,843 | B2 | 5/2019 | Berry et al. | |
| RE47,551 | E | 8/2019 | Jackson | |
| 10,368,916 | B2 | 8/2019 | May | |
| 10,413,333 | B2 | 9/2019 | Crossgrove et al. | |
| 10,441,319 | B2 | 10/2019 | Jackson et al. | |
| 10,499,958 | B2 | 12/2019 | Jackson | |
| 10,507,043 | B1 * | 12/2019 | Gladieux | A61B 17/8605 |
| 10,561,445 | B2 | 2/2020 | Jackson | |
| 10,603,082 | B2 | 3/2020 | Lish | |
| 10,617,447 | B2 | 4/2020 | Jackson | |
| 10,667,846 | B2 | 6/2020 | Ries et al. | |
| 10,702,310 | B2 | 7/2020 | Leff et al. | |
| 10,709,479 | B2 | 7/2020 | Keyer et al. | |
| 10,716,596 | B2 | 7/2020 | Gregory et al. | |
| 10,722,273 | B2 | 7/2020 | Jackson | |
| 10,729,468 | B2 | 8/2020 | Wilcox et al. | |
| 10,736,683 | B2 | 8/2020 | Garvey | |
| 10,751,127 | B2 | 8/2020 | Dace et al. | |
| 10,758,277 | B2 | 9/2020 | Schlaepfer et al. | |
| 10,765,455 | B2 | 9/2020 | Jackson et al. | |
| 10,765,456 | B2 | 9/2020 | Jackson et al. | |
| 10,779,863 | B2 | 9/2020 | Biedermann et al. | |
| 10,779,864 | B2 | 9/2020 | Jackson | |
| 10,799,272 | B2 | 10/2020 | Jackson | |
| 10,806,495 | B2 | 10/2020 | Jackson et al. | |
| 10,813,671 | B2 | 10/2020 | Jackson et al. | |
| 10,813,672 | B2 | 10/2020 | Jackson et al. | |
| 10,828,070 | B2 | 11/2020 | Ziemek et al. | |
| 10,856,911 | B2 | 12/2020 | Jackson et al. | |
| 10,874,438 | B2 | 12/2020 | Biester et al. | |
| 10,898,235 | B2 | 1/2021 | Biedermann et al. | |
| 10,918,420 | B2 | 2/2021 | Jackson et al. | |
| 10,966,759 | B2 | 4/2021 | Gregory | |
| 10,973,554 | B2 | 4/2021 | Biedermann et al. | |
| 10,973,555 | B2 | 4/2021 | Jackson et al. | |
| 10,987,139 | B2 | 4/2021 | Vedula et al. | |
| 11,013,536 | B2 | 5/2021 | Wickham et al. | |
| 11,020,150 | B1 | 6/2021 | Doubler et al. | |
| 11,020,152 | B2 | 6/2021 | Keyer et al. | |
| 11,026,723 | B2 | 6/2021 | Rezach et al. | |
| 11,026,730 | B2 | 6/2021 | Ramsay et al. | |
| 11,051,856 | B2 | 7/2021 | Jackson | |
| 11,065,065 | B2 | 7/2021 | Rezach | |
| 11,083,498 | B2 | 8/2021 | Biedermann et al. | |
| 11,083,501 | B2 | 8/2021 | Grizzard et al. | |
| 11,090,088 | B2 | 8/2021 | Biedermann | |
| 11,090,089 | B2 | 8/2021 | Biedermann et al. | |
| 11,090,090 | B2 | 8/2021 | Biedermann et al. | |
| 11,096,727 | B2 | 8/2021 | Barrus et al. | |
| 11,103,285 | B2 | 8/2021 | Dong et al. | |
| 11,103,286 | B2 | 8/2021 | Mishra et al. | |
| 11,109,895 | B2 | 9/2021 | May et al. | |
| 11,134,992 | B2 | 10/2021 | Schlaepfer et al. | |
| 11,141,199 | B1 | 10/2021 | Doubler et al. | |
| 11,147,592 | B2 | 10/2021 | Jackson et al. | |
| 11,147,594 | B1 | 10/2021 | Gladieux et al. | |

(56) References Cited

U.S. PATENT DOCUMENTS

| | | | |
|---|---|---|---|
| 11,154,331 B2 | 10/2021 | Toon et al. | |
| 11,160,581 B2 | 11/2021 | Jackson | |
| 11,160,582 B2 | 11/2021 | Biedermann et al. | |
| 11,166,751 B2 | 11/2021 | Shluzas et al. | |
| 11,172,961 B2 | 11/2021 | Yacoub et al. | |
| 11,185,349 B2 | 11/2021 | Jackson et al. | |
| 11,185,351 B2 | 11/2021 | Nelson | |
| 11,185,352 B2 | 11/2021 | Jackson et al. | |
| 11,191,571 B2 | 12/2021 | Biedermann et al. | |
| 11,191,573 B1 | 12/2021 | Leff et al. | |
| 11,197,693 B2 | 12/2021 | Biedermann et al. | |
| 11,197,696 B2 | 12/2021 | Jackson | |
| 11,219,470 B2 | 1/2022 | Avidano et al. | |
| 11,219,474 B2 | 1/2022 | Jackson | |
| 11,234,745 B2 | 2/2022 | Jackson | |
| 11,266,447 B2 | 3/2022 | Hawkes et al. | |
| 11,272,958 B2 | 3/2022 | Jackson | |
| 11,272,959 B2 | 3/2022 | Biedermann et al. | |
| 11,278,327 B2 | 3/2022 | Jackson | |
| 11,278,328 B2 | 3/2022 | Bas van der Pol | |
| 11,298,157 B2 | 4/2022 | Biedermann et al. | |
| 11,311,316 B2 | 4/2022 | Rezach et al. | |
| 11,333,192 B1 | 5/2022 | Lentner et al. | |
| 11,350,968 B2 | 6/2022 | Samuel et al. | |
| 11,350,970 B2 | 6/2022 | McKinley et al. | |
| 11,350,971 B2 | 6/2022 | Faulhaber | |
| 11,357,550 B2 | 6/2022 | Keyer et al. | |
| 11,369,417 B1 | 6/2022 | Linder et al. | |
| 11,369,418 B2 | 6/2022 | Biedermann et al. | |
| 11,369,419 B2 | 6/2022 | Mesiwala et al. | |
| 11,376,046 B1 | 7/2022 | Rezach | |
| 11,389,206 B2 | 7/2022 | Daniels | |
| 11,395,682 B2 | 7/2022 | Beyar et al. | |
| 11,395,684 B2 | 7/2022 | Gregory | |
| 11,406,427 B2 | 8/2022 | Nichols et al. | |
| 11,419,636 B2 | 8/2022 | Jackson et al. | |
| 11,426,208 B2 | 8/2022 | Jackson et al. | |
| 11,439,437 B1 | 9/2022 | Roberts et al. | |
| 11,439,438 B2 | 9/2022 | May | |
| 11,446,065 B2 | 9/2022 | Faulhaber | |
| 11,464,548 B2 | 10/2022 | Jackson et al. | |
| 11,464,549 B2 | 10/2022 | Jackson et al. | |
| 11,471,195 B2 | 10/2022 | Jackson et al. | |
| 11,484,346 B2 | 11/2022 | Jackson et al. | |
| 11,484,347 B2 | 11/2022 | Biedermann et al. | |
| 11,484,348 B2 | 11/2022 | Harvey et al. | |
| 11,490,931 B2 | 11/2022 | Casey et al. | |
| 11,497,532 B2 | 11/2022 | Jackson et al. | |
| 11,497,533 B2 | 11/2022 | Jackson et al. | |
| 11,504,164 B2 | 11/2022 | Jackson | |
| 11,510,711 B1 | 11/2022 | Robbins et al. | |
| 11,534,208 B2 | 12/2022 | Nichols et al. | |
| 11,534,222 B2 | 12/2022 | Murray | |
| 11,540,863 B2 | 1/2023 | Stoklund et al. | |
| 11,547,449 B2 | 1/2023 | Ramsay et al. | |
| 11,559,333 B2 | 1/2023 | Capote et al. | |
| 11,559,334 B2 | 1/2023 | May et al. | |
| 11,559,335 B2 | 1/2023 | Jackson et al. | |
| 11,564,715 B2 | 1/2023 | Biedermann et al. | |
| 11,571,244 B2 | 2/2023 | Loftis | |
| 11,576,708 B2 | 2/2023 | Lutz et al. | |
| 11,576,709 B2 | 2/2023 | Fessler et al. | |
| 2006/0241600 A1 | 10/2006 | Ensign | |
| 2006/0293664 A1* | 12/2006 | Schumacher ...... | A61B 17/7037 606/254 |
| 2007/0093826 A1 | 4/2007 | Hawkes et al. | |
| 2009/0005787 A1 | 1/2009 | Crall et al. | |
| 2009/0005815 A1 | 1/2009 | Ely | |
| 2009/0048634 A1 | 2/2009 | Jackson | |
| 2010/0114171 A1 | 5/2010 | Boachie-Adjei | |
| 2010/0160978 A1 | 6/2010 | Carbone | |
| 2010/0160980 A1 | 6/2010 | Walsh et al. | |
| 2010/0280554 A1 | 11/2010 | Vaidya | |
| 2011/0040338 A1 | 2/2011 | Jackson et al. | |
| 2011/0106173 A1 | 5/2011 | Lindemann et al. | |
| 2011/0202094 A1 | 8/2011 | Pereira et al. | |
| 2011/0270321 A1 | 11/2011 | Prevost et al. | |
| 2012/0035663 A1 | 2/2012 | Jackson et al. | |
| 2012/0041490 A1 | 2/2012 | Patrick et al. | |
| 2012/0203281 A1 | 8/2012 | Bouliane et al. | |
| 2013/0103092 A1 | 4/2013 | Ballard | |
| 2013/0103098 A1 | 4/2013 | Jackson et al. | |
| 2013/0138161 A1 | 5/2013 | Jackson | |
| 2014/0121703 A1 | 5/2014 | Jackson et al. | |
| 2014/0128927 A1 | 5/2014 | Jackson | |
| 2014/0336709 A1 | 11/2014 | Avidano et al. | |
| 2015/0250512 A1 | 9/2015 | Poker et al. | |
| 2015/0250521 A1 | 9/2015 | Poker et al. | |
| 2015/0272627 A1 | 10/2015 | Jackson | |
| 2015/0327889 A1 | 11/2015 | Jackson | |
| 2016/0113684 A1 | 4/2016 | Rezach et al. | |
| 2016/0262801 A1 | 9/2016 | Rezach et al. | |
| 2016/0361095 A1 | 12/2016 | Burdi et al. | |
| 2016/0361096 A1* | 12/2016 | van der Pol ....... | A61B 17/7076 |
| 2017/0020573 A1 | 1/2017 | Cain et al. | |
| 2017/0049482 A1 | 2/2017 | Campbell et al. | |
| 2017/0086886 A1 | 3/2017 | Duncan et al. | |
| 2017/0196610 A1 | 7/2017 | Jackson | |
| 2017/0245898 A1 | 8/2017 | May et al. | |
| 2018/0014858 A1* | 1/2018 | Biester ............... | A61B 17/7037 |
| 2018/0098797 A1 | 4/2018 | Jackson | |
| 2018/0368889 A1 | 12/2018 | Cole | |
| 2019/0069931 A1 | 3/2019 | Inceoglu | |
| 2019/0150988 A1 | 5/2019 | Jackson | |
| 2019/0223917 A1 | 7/2019 | Gray et al. | |
| 2020/0060731 A1 | 2/2020 | Richelsoph et al. | |
| 2020/0390472 A1 | 12/2020 | Detlefsen et al. | |
| 2020/0405362 A1 | 12/2020 | Faulhaber | |
| 2021/0169535 A1 | 6/2021 | Leff et al. | |
| 2021/0186571 A1 | 6/2021 | Jackson et al. | |
| 2021/0236174 A1 | 8/2021 | Jackson et al. | |
| 2021/0275230 A1 | 9/2021 | Jackson et al. | |
| 2021/0338295 A1 | 11/2021 | Jackson | |
| 2022/0008103 A1 | 1/2022 | McPhee | |
| 2022/0061892 A1 | 3/2022 | Jackson et al. | |
| 2022/0125484 A1 | 4/2022 | Jackson et al. | |
| 2022/0168018 A1 | 6/2022 | Jackson | |
| 2022/0168025 A1 | 6/2022 | Roth et al. | |
| 2022/0192715 A1 | 6/2022 | Rezach | |
| 2022/0226023 A1 | 7/2022 | Mast et al. | |
| 2022/0280202 A1 | 9/2022 | Mickiewicz et al. | |
| 2022/0313332 A1 | 10/2022 | Jackson et al. | |
| 2022/0330991 A1 | 10/2022 | Siedler | |
| 2022/0387081 A1 | 12/2022 | Jackson et al. | |
| 2023/0008092 A1 | 1/2023 | Jackson et al. | |
| 2023/0023180 A1 | 1/2023 | Jackson et al. | |
| 2023/0039383 A1 | 2/2023 | Jackson et al. | |

FOREIGN PATENT DOCUMENTS

| | | |
|---|---|---|
| EP | 2129310 B1 | 9/2012 |
| EP | 3610799 B1 | 4/2021 |
| EP | 2485654 B1 | 5/2021 |
| WO | 2008153723 A1 | 12/2008 |
| WO | 2009058318 A1 | 5/2009 |
| WO | 2011043805 A1 | 4/2011 |
| WO | 2011068516 A1 | 6/2011 |
| WO | 2011109009 A1 | 9/2011 |
| WO | 2012076005 A2 | 6/2012 |
| WO | 2016166163 A1 | 10/2016 |
| WO | 2018186887 A1 | 10/2018 |
| WO | 2019081438 A1 | 5/2019 |
| WO | 2020047269 A1 | 3/2020 |
| WO | 2021207674 A1 | 10/2021 |
| WO | 2022191707 A1 | 9/2022 |

* cited by examiner 300
301
301a
301b
302
303
304
305
307
310
311
313
315
316
317
320
321
322
323
323a
323b
324
324a
324b
324c
324d
324e
A
L
C
TD
CD
H2
D1
D2

SECTION A-A
A
A

POLYAXIAL SCREW ASSEMBLY

BACKGROUND

Spinal surgeries are typically employed to treat spinal conditions that result when functional segmental units of the spine are improperly aligned or otherwise damaged. Example spinal surgical procedures to treat spinal conditions include disc replacement, laminectomies, spinal fusion, spinal stabilization, vertebroplasty, kyphoplasty, and the like.

One aspect of certain spinal procedures, such as spinal fusion, is to mechanically stabilize the spine by preventing movement between the vertebrae while the bones of the spine heal. Such stabilization of the spine by securing the relevant bones during the healing process has greatly improved the success rate of spinal fusions and other procedures.

With spinal stabilization procedures, a combination of metal screws and rods may be used to create a bracing structure that holds the vertebrae in place. These devices are intended to prevent movement from occurring between the vertebrae. These stabilization components provide greater stability to the fusion site and allow the patient to be ambulatory much sooner.

In spinal surgery, for example, bone anchors can be used to secure a spinal fixation element to one or more vertebrae to rigidly or dynamically stabilize the spine in order to promote healing and potentially increased mobility for the patient.

During the spinal stabilization procedure, pedicle screws are typically placed through the pedicles on the posterior portion of two or more vertebrae of the spinal column. The screws gain purchase into the bone of the vertebral bodies, providing a secure hold on the vertebrae. Once the screws are placed on the vertebrae, they are attached to (typically metal) rods that connect all the screws together, producing an assembly that creates a stiff metal frame that holds the vertebrae in the desired arrangement and orientation so that healing can occur. The rods are placed into the upper opening of a polyaxial body, sometimes referred to as a "tulip" head. The upper portion of the polyaxial body contains a U-shaped opening into which the rod is placed. The lower portion of the polyaxial body receives an upper portion (e.g., the head) of the pedicle screw. The polyaxial body may rotate about the head of the pedicle screw to provide angulation thereabout. This angulation facilitates the placement and the contour of the rod that is necessary for the overall construct.

Some polyaxial assemblies exist that include a friction fit between the head of the pedicle screw and the lower portion of the tulip head. This is beneficial for several reasons, including the fact that surgeons prefer to have a tulip head that can temporarily maintain a given angulation, because this facilitates the placement therein of the rod. However, a need still exists for an improved friction fit between the tulip and the pedicle screw head. A need further exists for a tulip head that can grab or provide friction to pedicle screw heads that are smooth as well as to pedicle screw heads that are themselves threaded.

The following disclosed system, components, and methods help to meet these desired configurations and uses.

SUMMARY

The herein-described embodiments address these and other problems associated with the art by providing polyaxial screw assembly that includes a pop-on polyaxial screw head. The system includes a tulip head and a collet. The tulip head includes an upper portion to receive a rod and a lower portion to receive a pedicle screw. The lower portion includes multiple internal surface features for interacting with an external surface of the collet.

The collet interior may include an upper spherical interior surface above a lower spherical interior surface, with the lower spherical interior surface slightly undersized in diameter as compared to the upper spherical interior surface. The lower spherical interior surface is configured to wrap around the bottom of the shank head while the upper spherical interior surface is configured to receive the top of the shank head with less flexion. The collet may also include a plurality of vertical cuts or slits extending through the bottom of the collet to define a plurality of flexing/pivoting arms to allow flexibility of the arms. The collet may also have a hinge, for example in the form of a cut-out or groove either on the exterior diameter or on the interior diameter. The hinge serves to increase flexibility of the collet.

The collet may be rotated into position about a longitudinal axis within a horizontal groove below the threads of the tulip body and above the bottom of the U-shaped channel. The collet is then forced down from the assembly groove into a retention groove to allow vertical movement of the collet therein while constraining rotation. The bottom of the collet (e.g. arms) flexes outwardly to receive the shank head in an upper spherical interior (e.g. first stage) of the tulip body then is subsequently pushed vertically downwardly in the vertical/retention groove to position the arms of the lower spherical interior into a lower conical interior (e.g. second stage) of the tulip body smaller in diameter than the upper spherical interior. This second stage occurs when locking the construct down with a rod and a set screw and/or when an axial pulling force is applied to the polyaxial head.

In some embodiments, a polyaxial spinal fixation system comprises a polyaxial head having an upper section and a lower section, the upper section having two upstanding members with internal threading therein; the lower section having a collet cavity having a first section, a second section, and a third section. The first section includes a collet retention groove and an upper ledge at a top portion of the collet retention groove; the second section has a partially spherical concave surface; and the third section has a conical shape terminating in a lip. The system includes a bone fixation screw having a head and a threaded shank; a rod configured for insertion into the two upstanding members; and a set screw having threads thereon configured to mate with the internal threading of the polyaxial head. The system further includes a collet configured for insertion into the collet cavity. The collet further comprises a split-ring cylindrical body having a hinge thereon. The collet further comprises an upper portion and a lower portion, the upper portion including one or more tabs extending outwardly from an outer cylindrical surface, and the lower portion including multiple flanges separated by multiple slits. The flanges have an external surface having a partially spherical convex surface and a conical surface, and an internal surface having at least one partially spherical concave surface, a cylindrical surface, and a conical surface.

These and other advantages and features are set forth in the claims annexed hereto and forming a further part hereof. However, for a better understanding of the invention, and of the advantages and objectives attained through its use, reference should be made to the figures, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

It should be understood that the drawings are not necessarily to scale and that the embodiments are sometimes illustrated by graphic symbols, phantom lines, diagrammatic representations and fragmentary views. In certain instances, details that are not necessary for an understanding of the embodiments described and claimed herein, or which render other details difficult to perceive, may have been omitted. It should be understood, of course, that the scope of the claims is not to be limited to the particular embodiments illustrated in the figures. Indeed, it is expected that persons of ordinary skill in the art may devise a number of alternative configurations that are similar and equivalent to the embodiments shown and described herein without departing from the spirit and scope of the claims.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

For the purposes of this specification, the term "rod" is intended to refer to any elongated structure used for purposes of connecting items therealong, such as, for example, multiple vertebrae in a spinal column stabilization assembly. Such an elongated structure may be solid or hollow, straight or curved, and may have any desired cross-section (e.g., circular, oval, square, rectangular, hexagonal, irregular, etc.).

Further, for the purposes of this specification, the term "interference fit" is intended to refer to physical contact between two or more components whereby the components are securely coupled together. And, a "friction fit" is intended to refer to a physical contact between two or more components whereby the components are temporarily held in a particular orientation or arrangement, but that can be moved into a different orientation or arrangement by application of a relatively small threshold force input.

The embodiments described herein allow engagement of the pedicle screw in the accommodating head either before or after the pedicle screw has been inserted into bone.

Figure 1B:
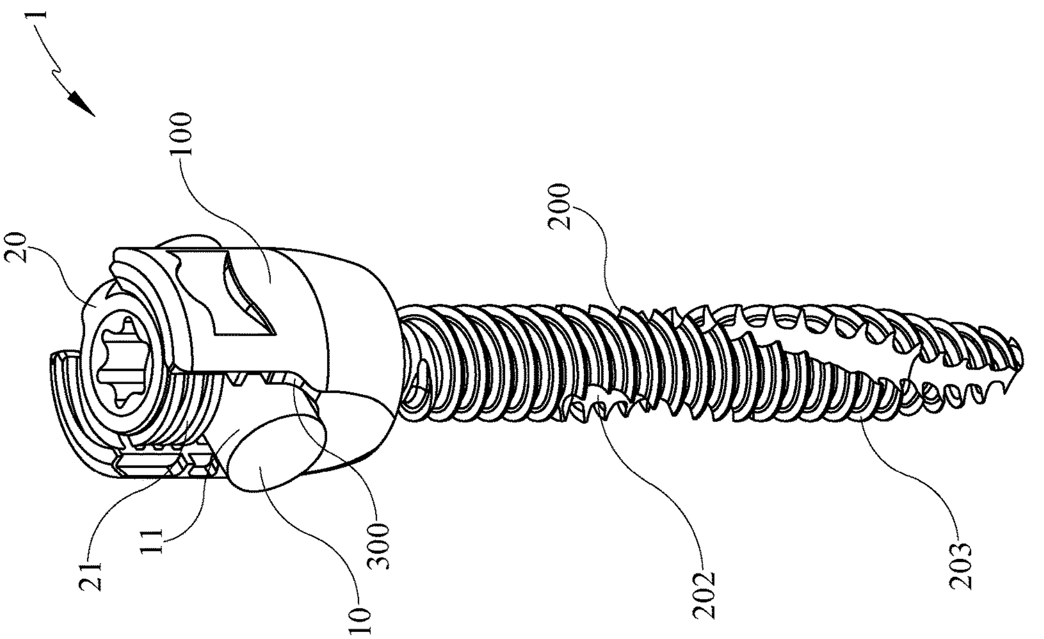
FIG. 1B is a perspective view of a portion of a polyaxial spinal implant assembly according to an embodiment.
Figure 1A:
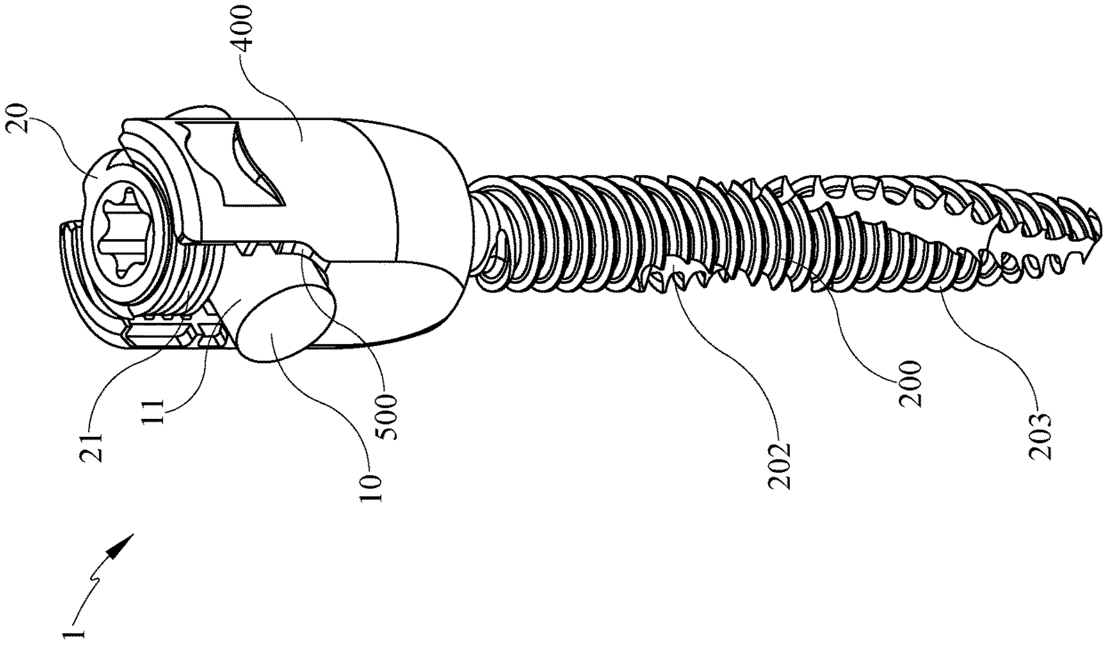
FIG. 1A is a perspective view of a portion of a polyaxial spinal implant assembly according to an embodiment.
Figure 2A:
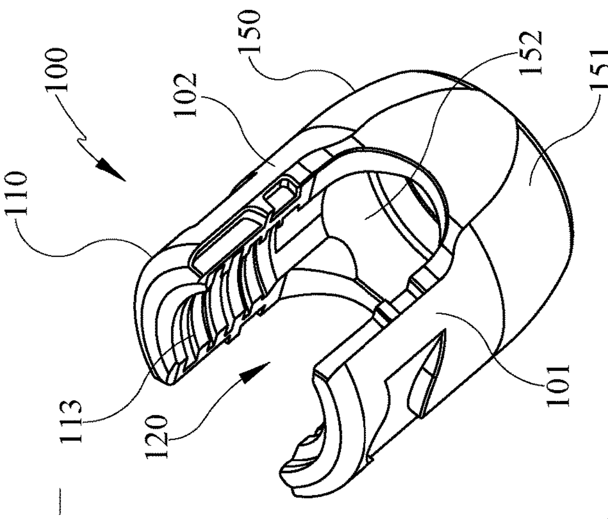
FIG. 2A is a perspective view of polyaxial head according to an embodiment.
Figure 2B:
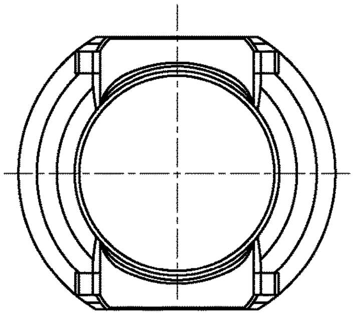
FIG. 2B is a bottom view of the polyaxial head of FIG. 2A.
Figure 2C:
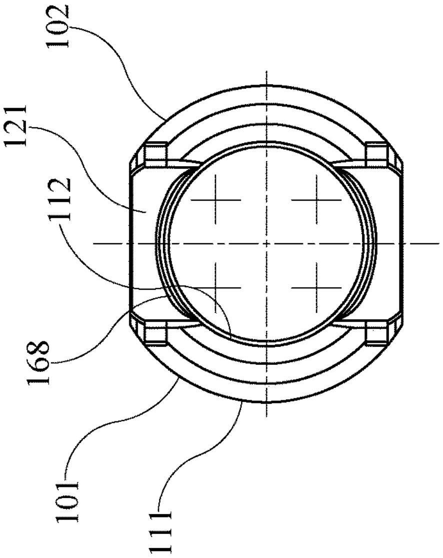
FIG. 2C is a top view of the polyaxial head of FIG. 2A.
Figure 2D:
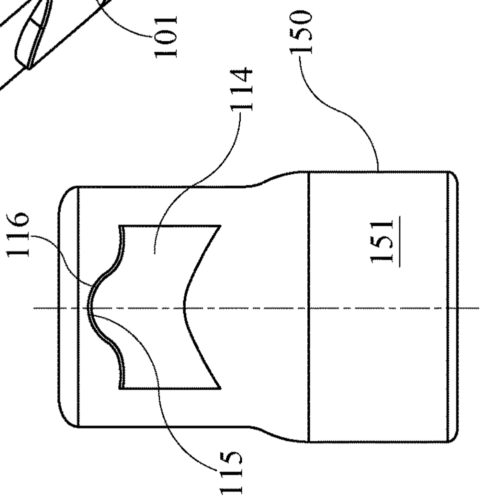
FIG. 2D is a left side view of the polyaxial head of FIG. 2A.
Figure 2E:
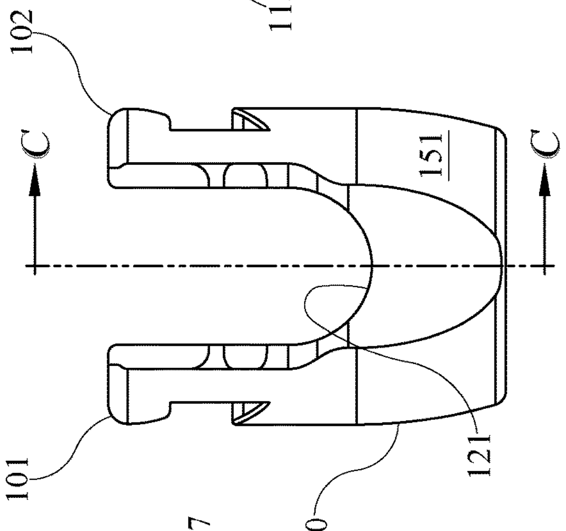
FIG. 2E is a front view of the polyaxial head of FIG. 2A.
Figure 2F:
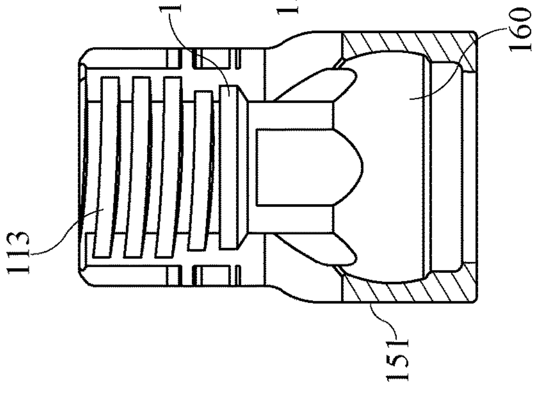
FIG. 2F is a section view taken at line C-C of FIG. 2E.
Figures 7A, 7B, 7C:
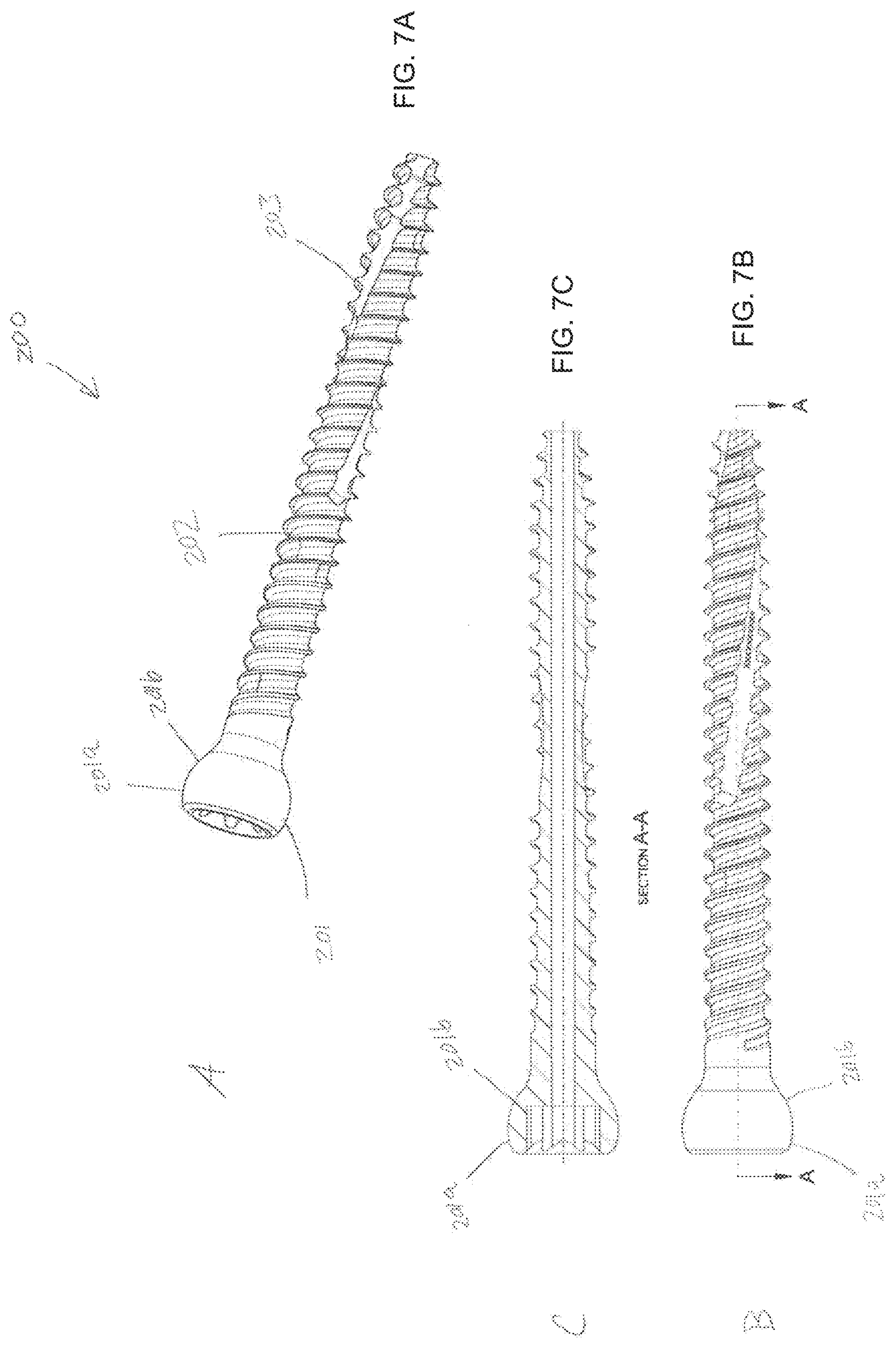
FIG. 7A is a perspective view of a bone fixation screw according to an embodiment.
FIG. 7B is a side view of the bone fixation screw of FIG. 7A.
FIG. 7C is a section view of the bone fixation screw taken at line A-A of FIG. 7B.
Figure 8A:
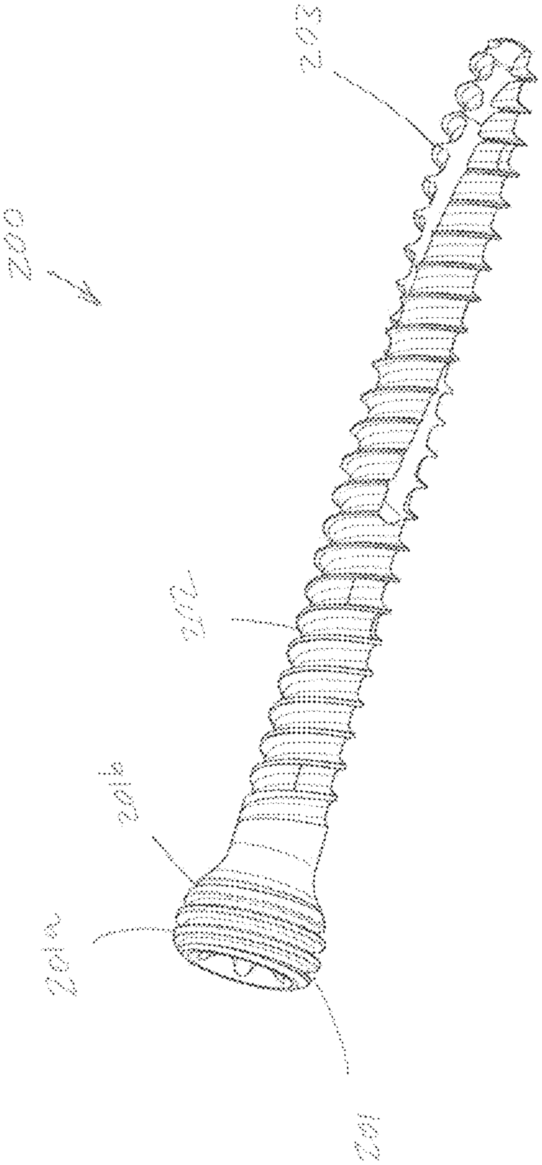
FIG. 8A is a perspective view of a bone fixation screw according to another embodiment.
Figure 8C:
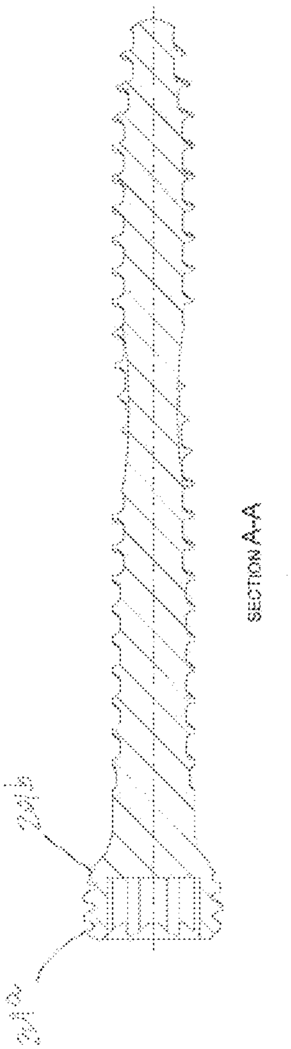
FIG. 8C is a section view of the bone fixation screw taken at line A-A of FIG. 8B.
Figure 8B:
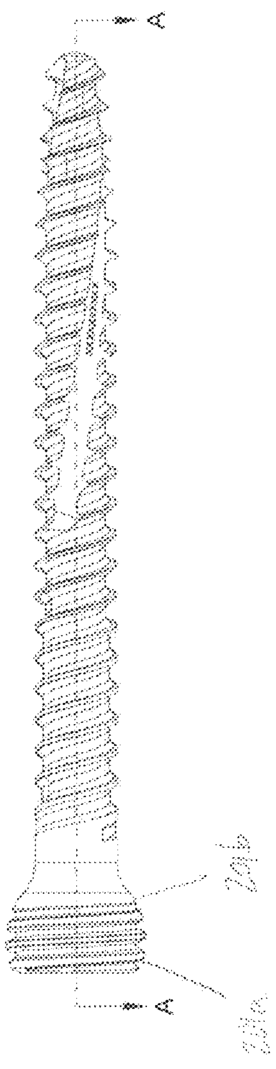
FIG. 8B is a side view of the bone fixation screw of FIG. 8A.

Turning now to the drawings, wherein like numbers denote like parts throughout the several views, FIGS. 1A and 1B illustrate a perspective view of a polyaxial screw assembly system 1 according to an embodiment that includes a rod 10; a set screw 20; a polyaxial head 100; a bone fixation screw 200; and a collet 300. The rod 10 has an outer surface 11. The set screw 20 has external threads 21. The bone fixation screw 200 can take many forms, and typically comprises a head 201 and a shank 202 comprising male threads 203. The head 201 can be smooth or threaded and can take many shapes (for example, spherical, partially spherical, truncated curvate, and other commonly known types of heads for polyaxial bone screws). The shank 202 can be solid, cannulated, fenestrated, or combinations (either complete or partial) thereof. FIGS. 7A-7C depict one embodiment of a bone fixation screw 200 having a smooth head 201 and being cannulated. FIG. 8A-8C depict another embodiment of a bone fixation screw 200 having a threaded head 201 and being solid (i.e., not cannulated). In the embodiments shown in the figures, the head 201 is partially spherical and includes an upper hemisphere 201*a* and a lower hemisphere 201*b*. The male threads 203 can be of any common thread form for polyaxial bone screws.

FIGS. 2A-2F and 3A-F depict a polyaxial head 100 according to an embodiment. The polyaxial head 100 takes the form of a modified cylinder and includes an upper portion 110 with internal threads 113 and a lower portion

150. The polyaxial head 100 comprises two upstanding members 101 and 102 separated by a U-shaped channel 120. The internal threads 113 are formed on the inside of each upstanding member 101, 102 and define an inner thread diameter ITD. The internal threads 113 extend from the top of the upstanding members 101, 102 toward the bottom of the polyaxial head 100 for a given thread depth. For purposes of this description, the upper portion 110 refers generically to that portion of the polyaxial head 100 that includes the upstanding members 101, 102 and the internal threads 113. With reference again to FIG. 1, the rod 10 is secured within the U-shaped channel 120 in the upper portion 110 of the polyaxial head 100 between the upstanding members 101, 102 via the set screw 20. In polyaxial screw assembly system 1 using embodiments as described herein, one or more rods 10 and multiple polyaxial heads 100 can be used to secure a spinal column.

With continued reference to FIGS. 2A-2F and 3A-3F, the upper portion 110 has an external surface 111 and an internal surface 112, both of which are bifurcated by the U-shaped channel 120. The external surface 111 of the upper portion 110 includes an indented portion 114 having a chevron 115. The chevron 115 can have one or more undercuts 116 and can be used to facilitate connection to various tools. The U-shaped channel 120 has a bottom surface 121 against which the outer surface 11 of the rod 10 can bear. The internal surface 112 of the upper portion 110 includes internal threads 113 configured to receive complementary external threads 21 on the set screw 20. The lead internal thread 113 can, of course, be tapered or chamfered to facilitate ease of entry of the set screw 20. The type of thread form that makes up the internal threads 113 can be any of the commonly understood shapes suitable for such applications, including, without limitation, square threads, buttress threads, reverse-angle threads, and many others.

The lower portion 150 of the polyaxial head 100 includes an external surface 151 and an internal surface 152. The internal surface 152 includes several unique features and sections within the lower portion 150 that are configured to interact with an external surface of the collet 300 (described below) and to provide the desired functionality of the collet 300 with respect to the bone fixation screw 200. The internal surface 152 includes a collet cavity 160 having a height H1.

FIGS. 4A-4E depict a collet 300 according to an embodiment. The collet 300 is an overall modified cylindrical ring-like body having particular features configured to facilitate the desired functionality of the assembly. The collet 300 is configured to be placed within the internal surface 152 of the lower portion 150 as will be described below. The collet 300 includes a body 301 having a first side 301*a*, a second side 301*b*, and a height H2, wherein the body 301 takes the basic shape, when viewed from a top view as in FIG. 4B, of a split ring having a separation 302. The first side 301*a* is separated from the second side 301*b* at separation 302. Thus, separation 302 creates a first face 303 on first side 301*a* and a second face 304 on the second side 301*b* in opposing arrangement with respect to each other.

The body 301 includes an upper portion 310 and a lower portion 320. The upper portion 310 includes an external surface 311 defining an external perimeter 312 and an internal surface 313 defining an internal perimeter 314. The distance between the external surface 311 and the internal surface 313 is first thickness 315. The upper portion 310 further includes an upper surface 316. A portion of the upper surface 316 lies in a plane perpendicular to an axis "A" through a longitudinal center "C" of the body 301. Another portion of the upper surface 316 is concavely curved rod surface 305 configured to receive an outer surface 11 of a rod 10. The rod surface 305 has a longitudinal axis "L" perpendicular to axis A and intersecting axis A.

Diametrically opposed to the separation 302 is a hinge 307. The hinge 307 connects first side 301*a* and second side 301*b*. That is, whereas the first side 301*a* and second side 301*b* are separated at separation 302, the first side 301*a* and second side 301*b* are joined at hinge 307. The external surface 311 of the upper portion 310 assumes a primarily cylindrical form having a cylindrical diameter "CD". However, one or more tabs 317 is located at the upper portion 310, preferably, though not necessarily, at the upper surface 316. Tabs 317 extend radially outwardly beyond the cylindrical diameter CD of the upper portion 310. That is, the outer distance spanning across the tabs 317, referred to herein as the tab diameter "TD", is greater than the cylindrical diameter CD of the cylindrical portion of the body 301. The purpose of the tabs 317 will be described below.

With continued reference to FIGS. 4A-4E, the lower portion 320 begins at a lower end of the cylindrical external surface 311 of the upper portion 310. The lower portion 320 includes a series of flanges 321 separated by slits 322. The slits 322 are arranged parallel to the axis A of the body 301 and disposed circumferentially about the body 301. One or more, or all, of the slits 322 extend beyond the lower portion 320 and into the upper portion 310.

Each flange 321 has an external surface 323 and an internal surface 324. The external surface 323 includes a first section 323*a* and a second section 323*b*. The first section 323*a* has a partially spherical convex outer surface. The second section 323*b* has a conical outer surface. The conical outer surface of the second section 323*b* acts as a wedging surface when interacting with certain portions of the polyaxial head 100, as will be discussed later.

The internal surface 324 of each flange 321 has multiple sections, each with a different shape. A first section 324*a* has a partially spherical concave surface having a first radius R1. A second section 324*b*, adjacent to the first section 324*a*, has a partially spherical concave surface having a second radius R2. The radii R1 and R2 can be the same or different, and similarly can be offset or coincident. In the embodiment shown, the second radius R2 is slightly smaller (undersized) than the first radius R1. Additionally, in an alternative embodiment not shown in the figures, a cylindrical section can be present between the spherical first section 324*a* and the spherical second section 324*b*. A third section 324*c*, adjacent to the second section 324*b*, has a transition surface to transition from the partially spherical surface of the second section 324*b* to the cylindrical surface of fourth section 324*d*. As stated, fourth section 324*d*, adjacent to the third section 324*c*, has a cylindrical surface having a diameter D1. A fifth section 324*e*, adjacent to the fourth section 324*d*, has a conical surface. A diameter D2 of the fifth section 324*e* nearest the lower end of the fifth section 324*e* is greater than diameter D1. The larger diameter of D2 facilitates the receipt, within the fifth section 324*e*, of the head of the bone fixation screw 200, as will be described below.

FIGS. 5A-5C and 6A-6C depict the collet 300 in various stages of insertion into the polyaxial head 100. The collet 300 can be inserted into the polyaxial head 100 from above, that is, from the top of the polyaxial head 100 past the internal threads 113. The polyaxial head 100 and the collet 300 each contain certain geometric features that facilitate not only the insertion of the collet 300 into the polyaxial head 100, but also the proper retention of the collet 300 therein.

Figures 3A, 3B, 3C, 3D, 3E, 3F:
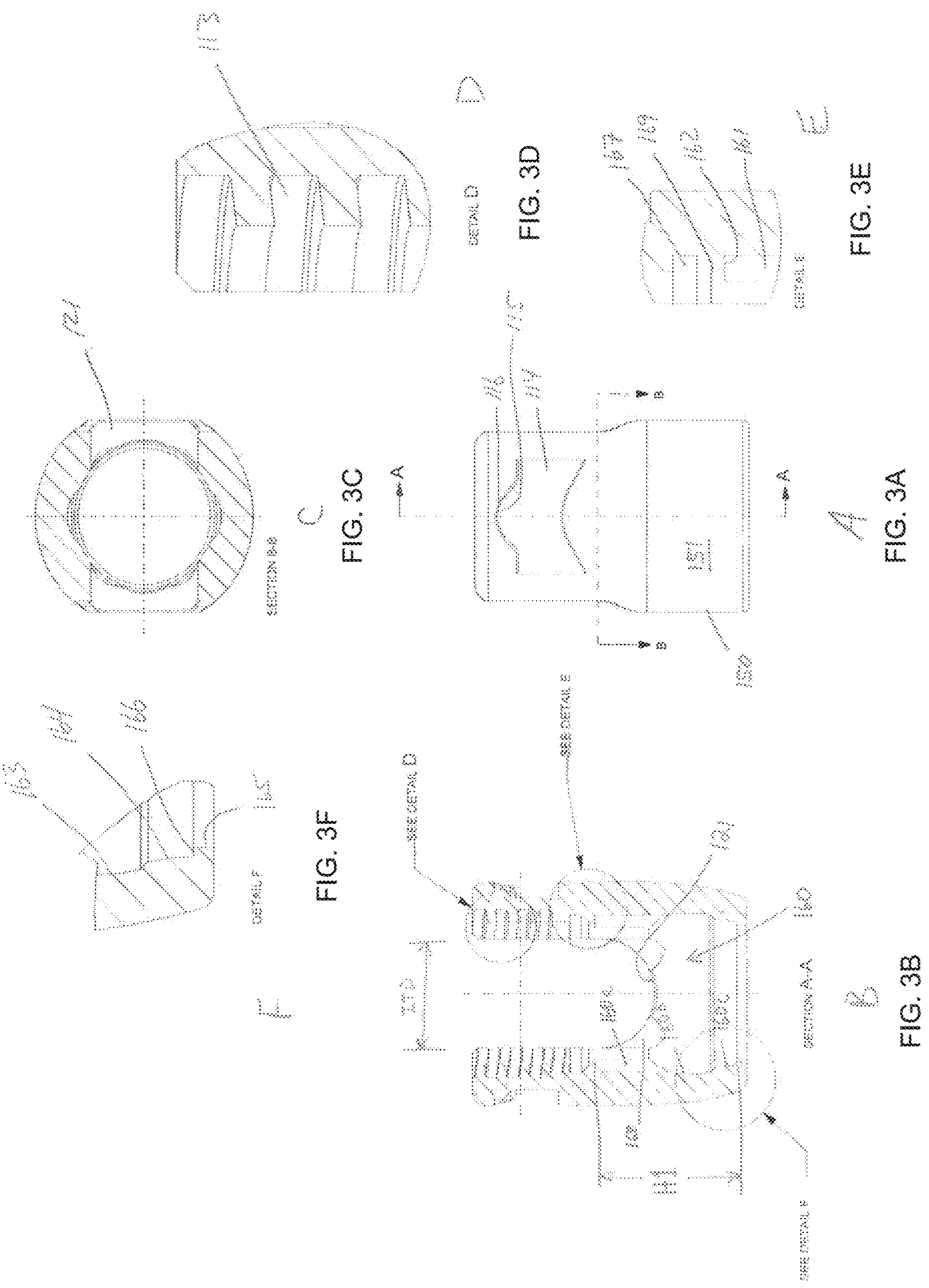
FIG. 3A is a right side view of the polyaxial head of FIG. 2A.
FIG. 3B is a section view taken at line A-A of FIG. 3A.
FIG. 3C is a section view taken at line B-B of FIG. 3A.
FIG. 3D is a detail view of Detail D from FIG. 3B.
FIG. 3E is a detail view of Detail E from FIG. 3B.
FIG. 3F is a detail view of Detail F from FIG. 3B.
Figures 4A, 4B, 4C, 4D, 4E:
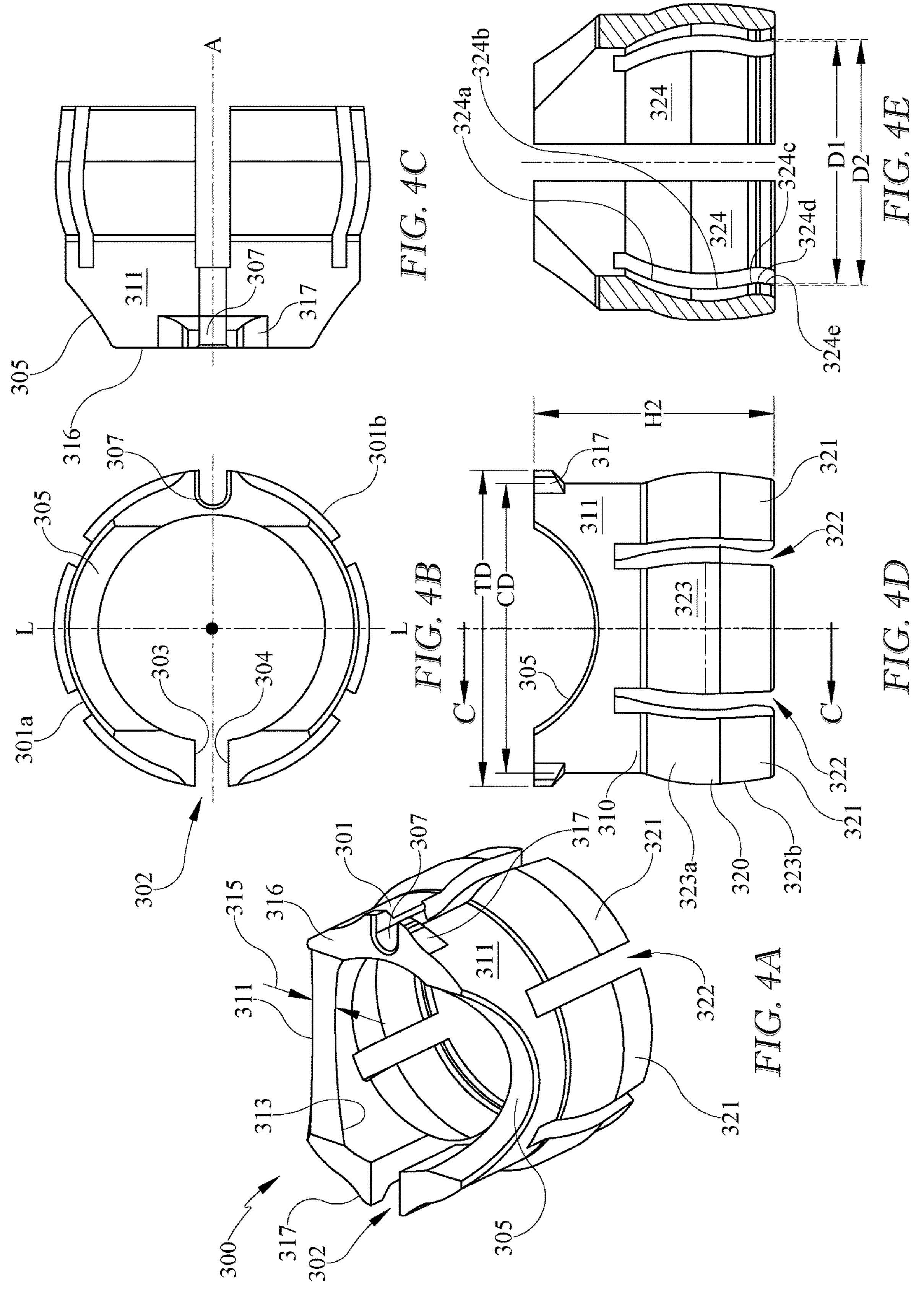
FIG. 4A is a perspective view of a collet according to an embodiment.
FIG. 4B is a top view of the collet of FIG. 4A.
FIG. 4C is a side view of the collet of FIG. 4A.
FIG. 4D is a front view of the collet of FIG. 4A.
FIG. 4E is a section view taken at line C-C of FIG. 4D.

Referring again to FIGS. 2A-2F and 3A-3F, the lower portion 150 contains several sections therein having differing surface shapes and dimensions for particular reasons. Beneath the internal threads 113 in the lower portion 150 is the collet cavity 160. The collet cavity 160 has an upper portion 160*a*, a middle portion 160*b*, and a lower portion 160*c* (FIG. 3B). A collet assembly groove 167 exists in the upper portion 160*a* in the upstanding members 101, 102 (FIG. 3D). The collet assembly groove 167 has a collet assembly groove diameter "CAGD" that is greater than the tab diameter TD. A collet retention groove 161 exists in the upper portion 160*a* in the upstanding members 101, 102 (FIG. 3E) below the collet assembly groove 167. The collet assembly groove 167 and the collet retention groove 161 are separated by a lip of some thickness, collet retention lip 169. The collet retention groove 161 has an upper ledge 162 at its upper extremity. The collet retention groove 161 has a collet groove diameter "CGW" that is greater than the tab diameter TD. The collet retention groove 161 has a diameter that is not coaxial with the central axis of the polyaxial head 100. The collet retention groove 161 may be cut into one or both upstanding members 101, 102. The collet retention groove 161 and upper ledge 162 prevent rotation of the collet 300. The collet assembly groove 167 allows the collet 300 to be rotated into the polyaxial head 100 during assembly.

The middle portion 160*b* comprises a spherical surface having a diameter large enough to accept the cylindrical diameter CD of the upper portion 310 of the body 301. Extending from the upper portion 160*a* into the middle portion 160*b* are relief cuts 168. In the embodiment shown, four relief cuts 168 are included, though there can be zero or a plurality of relief cuts 168. The relief cuts 168 have a diameter "RD" that is not coaxial with the central axis of the polyaxial head 100.

The lower portion 160*c* has several portions therein, each having different surface shapes and dimensions (FIG. 3F). A first section 163 at the upper end of the lower portion 160*c* has a partially spherical concave surface having a cavity radius "CR". Below the first section 163 is a second section 164. Second section 164 has a conical surface with a larger diameter adjacent the first section 163. The cone angle of the depicted embodiment is approximately 13 degrees, but could be anywhere from approximately 4 degrees to approximately 45 degrees. This conical surface provides a wedging force against the conical surface of the second section 323*b* of each flange 321. A third section 165 resides adjacent the second section 164 and provides the exit from the polyaxial head 100. The third section 165 is cylindrical and has a diameter smaller than the diameter of the bottom portion of the conical surface of second section 164. This creates a lip 166 at the junction of the second section 164 and third section 165.

Various methods of implantation of the polyaxial screw assembly system 1 are enabled according to the embodiments described. As stated above, the collet 300 and polyaxial head 100 sub-assembly can snap onto the head 201 of a bone fixation screw 200 either before or after the bone fixation screw 200 has been implanted in bone. This provides several options for methods of implantation and the concomitant kits provided to the surgeon therefor. One option provides each of the components (e.g., rods 10, set screws 20, polyaxial heads 100, bone fixation screws 200, and collets 300) as individual items in the surgical kit for the surgical staff to assemble, as desired. Another option enables the pre-assembly of the collet 300 into the polyaxial head 100, either by the manufacturer when the kit is prepared or by the surgical staff on the back table. In either of these two options, the surgeon can implant the bone fixation screw 200 into the bone first, and can then pop on to the bone fixation screw 200 the sub-assembly of the collet 300 and polyaxial head 100. Another option involves pre-assembling the three components: bone fixation screw 200, the collet 300, and the polyaxial head 100. This pre-assembly can be done at the time the kit is prepared, or can be done on the back table in the surgical room. With this pre-assembly, when the surgeon implants the bone fixation screw 200 into the bone, the collet 300 and the polyaxial head 100 are already coupled to the bone fixation screw 200. Because the body 301 of the collet 300 is an open cylinder, the insertion tool used by the surgeon for implanting the bone fixation screw 200 can easily pass through the collet 300 and into the head 201 of the bone fixation screw 200.

Figure 5C:
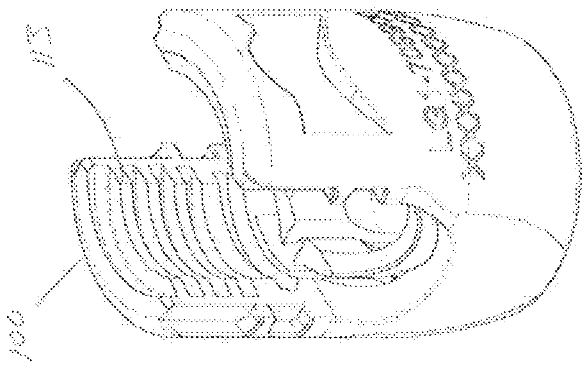
FIG. 5C is a perspective view of a collet and polyaxial head subassembly in a third stage of collet insertion.
Figure 5B:
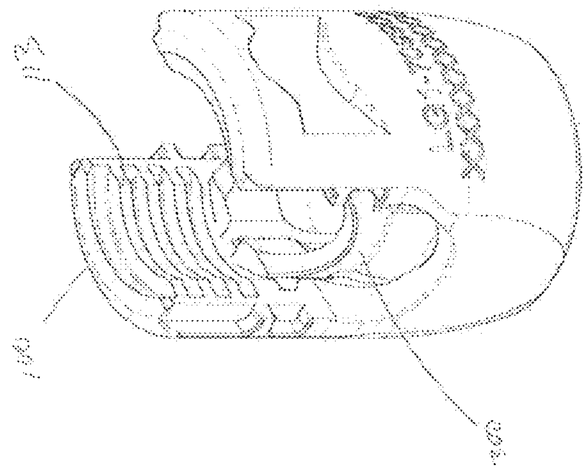
FIG. 5B is a perspective view of a collet and polyaxial head subassembly in a second stage of collet insertion.
Figure 5A:
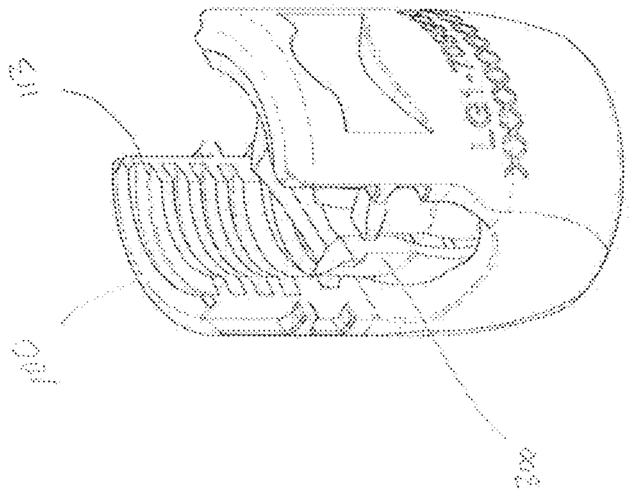
FIG. 5A is a perspective view of a collet and polyaxial head subassembly in a first stage of collet insertion.
Figure 6B:
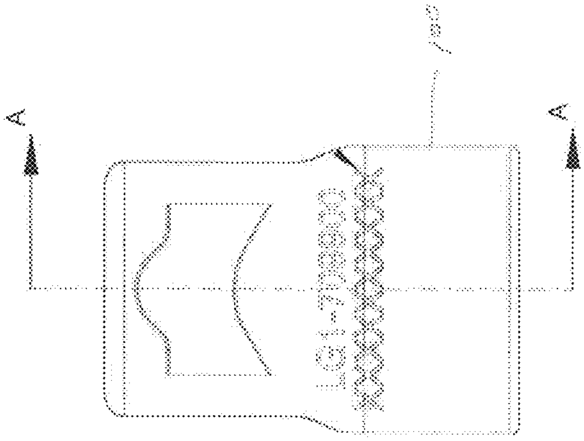
FIG. 6B is a right side view of a collet and polyaxial head subassembly.
Figure 6C:
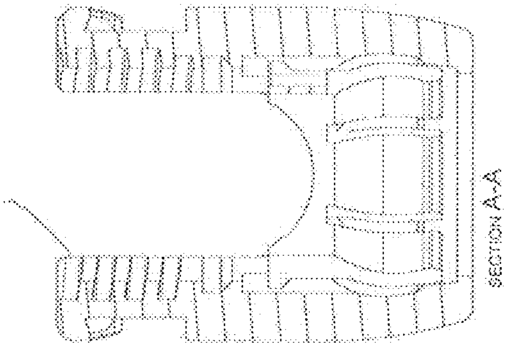
FIG. 6C is a section view of the collet and polyaxial head subassembly taken at line A-A of FIG. 6B.
Figure 6A:
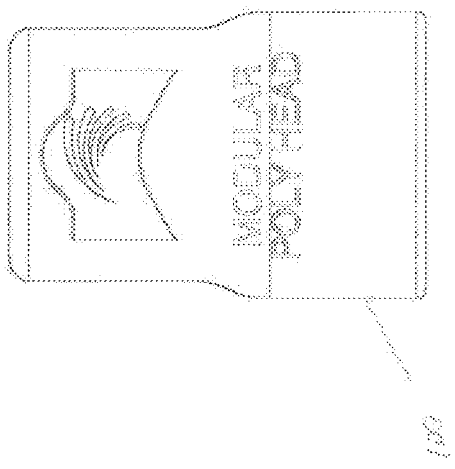
FIG. 6A is a left side view of a collet and polyaxial head subassembly.

Referring again to FIGS. 5A-5C and 6A-6C, the installation of the collet 300 into the polyaxial head 100 is shown. As stated above, the cylindrical diameter CD of the body 301 of the collet 300 is less than the inner thread diameter ITD of the upstanding members 101, 102 of the polyaxial head 100. However, the tab diameter TD is greater than the inner thread diameter ITD. Therefore, to insert the collet 300 into the polyaxial head 100, the body 301 must be turned so that the tabs 317 align with the U-shaped channel 120 (FIG. 5A). Because the cylindrical diameter CD of the body 301 is less than the inner thread diameter ITD of the upstanding members 101, 102, the body 301 of the collet 300 can be inserted into the polyaxial head 100 from the top and pushed down toward the bottom of the body 301. As the external surface 323 of the collet 300 has a larger diameter than the cylindrical diameter CD, compression of the flanges 321, hinge 307, and separation 302 must occur as the collet 300 is pushed toward the bottom of the lower portion 150. As the collet 300 is pushed into polyaxial head 100, the flanges 321 pass through relief cuts 168, aiding in compression of the external surface 323. Once the collet 300 is pushed far enough into the polyaxial head 100 so as to align the tabs 317 with the collet assembly groove 167 of the collet cavity 160, the collet 300 can be rotated (approximately 90 degrees in the embodiment shown in the figures) to position the tabs 317 in line with the collet retention groove 161 (FIG. 5B). This can be done preferably with the aid of a tool. One such tool could be a short rod-shaped body that fits in the rod channel on the end of a stick. The upper ledge 162 serves to prevent the collet 300 from becoming dislodged from the polyaxial head 100 by providing a blocking surface against which the upper surface 316 of the tabs 317 interact. Once the collet 300 is rotated and forced down such that the tabs 317 reside within the collet retention groove 161 beneath the upper ledge 162, the collet 300 can then translate farther downwardly within the collet cavity 160 because the collet cavity 160 has a collet cavity height H1 that is greater than the height H2 of the collet 300 (FIG. 5C). The collet retention groove 161 controls rotation of the collet 300 while allowing axial translation between upper ledge 162 and lip 166.

Various features of the collet 300 provide the flexibility of the collet 300 to enable this pop-on ability. First, the slits 322 that separate the flanges 321 provide flexibility, allowing some measure of expansion of the collet 300 as the head 201 of the bone fixation screw 200 is forced into the lower portion 320 from below. Second, the hinge 307 provides the only circumferential connection between the first side 301*a* and the second side 301*b*, so the body 301 is able to pivot (that is, expand and contract) about the hinge 307. This combination of hinge 307 and separation 302 provides a collet 300 with significantly increased flexibility. The hinge 307 of the embodiment shown in the figures faces outwardly, but could alternatively be formed to face inwardly as well. Similarly, the hinge 307 can be oriented as being in line with the tabs 317 (as shown in the figures), or it can be oriented in any rotational position about the central axis A of the collet 300.

During the pop-on procedure, the flanges 321 temporarily expand in diameter to allow the head 201 of the bone fixation screw 200 to first enter the fifth section 324*e* of the lower portion 320. Because the head 201 is spherical, there is a portion of the head 201 that can enter the fifth section 324*e* without causing expansion. When the fifth section 324*e* abuts the fourth section 324*d*, the collet 300 is forced up against the upper ledge 162 until translation is prevented, then the collet 300 flexes open and accepts the head 201. The diameter D2 of the fifth section 324*e* is smaller than the diameter of the head 201 of the bone fixation screw 200. As the collet 300 is continued to be pushed onto the bone fixation screw 200, the head 201 next enters the fourth section 324*d*. The diameter D1 of the fourth section 324*d* is smaller than diameter D2, and also smaller than the diameter of the head 201. As a result, the flanges 321, splay outwardly to increase in internal diameter such that the head 201 can be moved into and then past the cylindrical surface of the fourth section 324*d*. Once the head 201 is past the fourth section 324*d*, the head 201 enters the third section 324*c* that is a transition to the second section 324*b*. Once the head 201 is inside the second section 324*b*, the lower portion of the flanges 321 are in contact with the lower hemisphere 201*b* of the head 201, while the upper portion of the flanges 321 are in at least partial contact with at least a portion of the upper hemisphere 201*a* of the head 201. Because the radius R2 of the second section 324*b* is undersized compared to the radius R1 of the first section 324*a*, the second section 324*b* grabs the lower hemisphere 201*b* of the head 201 with a higher degree of friction than does the first section 324*a* grab the upper hemisphere 201*a* of the head 201. The head 201 can be any style of head 201, including smooth or threaded, and can be properly frictionally held because of the way the flanges 321 and hinge 307 flex. The upper portion of the flanges 321 is closer to the point of origin of the where the flexion occurs, so for the same angulation, less change in spherical diameter will be experienced here. By increasing the spherical diameter in the first section 324*a*, flexion in the flanges 321 is driven lower in the internal surface 324, as the first point of interference between the shank head 201 and the internal surface 324 occurs lower. Driving flexion lower in the internal surface 324 reduces the amount of bowing that occurs in the collet 300 as the second section 323*b* of the external surface 323 of the collet 300 is forced in contact with the second section 164 of the lower portion 160*c* of the polyaxial head 100. Driving flexion lower in the internal surface 324 also causes more gripping to occur on the lower hemisphere 201*b* of the head 201 than the upper hemisphere 201*a* of the head 201. This provides beneficial increased pull-off strength of the polyaxial screw assembly system 1 when it is locked down.

To lock down the polyaxial screw assembly system 1, a rod 10 is inserted into the U-shaped channel 120 of the polyaxial head 100. In typical surgical applications, multiple bone fixation screws 200 will be implanted, and thus multiple polyaxial heads 100 will be upstanding from the bone fixation screws 200 into which a rod 10 is inserted that spans the desired length of the polyaxial screw assembly system 1 (see FIG. 1). A set screw 20 is inserted into the tops of each polyaxial head 100 to keep the rod 10 inside the polyaxial head 100. Each set screw 20 is rotated such that the external threads 21 engage the internal threads 113 of the upper portion 110 of the polyaxial head 100. As the set screws 20 are tightened, they force the rod 10 into contact with the rod surface 305 of the upper surface 316 of the collet 300. Upon further tightening of the set screw 20, the rod 10 pushes on the rod surface 305 and moves the collet 300 downwardly farther into the collet cavity 160. As this happens, the second section 323*b* of the external surface 323 of the collet 300 is pushed into forcible contact with the second section 164 of the collet cavity 160. The complementary conical surfaces of the second section 164 and the second section 323*b* create a flat-to-flat contact that provides a wedging action as the downward force is applied to the collet 300 by the rod 10. This wedging action compresses the flanges 321 around the head 201 of the bone fixation screw 200. Upon final tightening of the set screw 20, the compression of the collet 300 securely fixes the angular orientation of the bone fixation screw 200 with respect to the polyaxial head 100.

Further aspects of the embodiments described herein are provided by the subject matter of the following clauses:

Clause 1—A polyaxial spinal fixation system comprising: a polyaxial head having an upper section and a lower section, the upper section having two upstanding members comprising internal threading therein; the lower section having a collet cavity having a first section, a second section, and a third section; wherein the first section includes a collet retention groove and an upper ledge at a top portion of the collet retention groove; the second section has a partially spherical concave surface; and the third section has a conical shape terminating in a lip; a bone fixation screw having a head and a threaded shank; a rod configured for insertion into the two upstanding members; a set screw having threads thereon configured to mate with the internal threading of the polyaxial head; and a collet configured for insertion into the collet cavity, wherein the collet further comprises a split-ring cylindrical body having a hinge thereon, and wherein the collet further comprises an upper portion and a lower portion, the upper portion including one or more tabs extending outwardly from an outer cylindrical surface, and the lower portion including multiple flanges separated by multiple slits, each flange of the multiple flanges having an external surface having a partially spherical convex surface and a conical surface, and an internal surface having at least one partially spherical concave surface, a cylindrical surface, and a conical surface.

Clause 2—The polyaxial spinal fixation system of any preceding clause, wherein the two upstanding members of the upper section define a U-shaped channel.

Clause 3—The polyaxial spinal fixation system of any preceding clause, wherein the rod is secured within the U-shaped channel by the set screw.

Clause 4—The polyaxial spinal fixation system of any preceding clause, wherein the internal threading is tapered or chamfered to facilitate ease of entry of the set screw.

Clause 5—The polyaxial spinal fixation system of any preceding clause, wherein the split-ring cylindrical body further comprises a first side and a second side, wherein the first side and the second side are joined at the hinge.

Clause 6—The polyaxial spinal fixation system of any preceding clause, wherein the slits are arranged parallel to a vertical axis of the split-ring cylindrical body and disposed circumferentially about the split-ring cylindrical body.

Clause 7—The polyaxial spinal fixation system of any preceding clause, wherein one or more of the slits extends beyond the lower portion and into the upper portion of the collet.

Clause 8—The polyaxial spinal fixation system of any preceding clause, wherein the internal surface of at least one flange comprises a first partially spherical concave surface with a first radius and a second partially spherical concave surface with a second radius, wherein the second radius is smaller than the first radius.

Clause 9—The polyaxial spinal fixation system of any preceding clause, further comprising a collet assembly groove comprising a collet assembly groove diameter that is greater than a tab diameter.

Clause 10—The polyaxial spinal fixation system of any preceding clause, wherein the collet retention groove is positioned below the collet assembly groove and the collet retention groove has a collet groove diameter that is greater than the tab diameter.

Clause 11—The polyaxial spinal fixation system of any preceding clause, wherein a collet retention groove diameter is not coaxial with a central axis of the polyaxial head.

Clause 12—The polyaxial spinal fixation system of any preceding clause, wherein the second section comprises a conical surface with a second section diameter that is larger than a first section diameter of the first section.

Clause 13—The polyaxial spinal fixation system of any preceding clause, wherein the third section comprises a cylindrical surface having a third section diameter smaller than the second section diameter to define the lip at a junction of the second section and the third section.

Clause 14—A method for installing a polyaxial spinal fixation system comprising: inserting a bone fixation screw using an insertion tool; installing a collet into a collet cavity of a lower section of a polyaxial head; rotating the collet within the collet cavity to position one or more tabs within a collet retention groove but below an upper ledge to limit rotation of the collet within the polyaxial head; selectively translating the collet within the collet cavity between the upper ledge and a lip; attaching the collet to the bone fixation screw by contacting a lower portion of the collet having multiple flanges with the head of the bone fixation screw such that the multiple flanges splay outwardly to accept the head within the lower portion wherein a first portion of each flange at least partially contacts a lower hemisphere of the head and a second portion of each flange at least partial contacts an upper hemisphere of the head to frictionally hold the head of the bone fixation screw within the collet; inserting a rod into a U-shaped channel of the polyaxial head; installing a set screw to engage with an internal threading within an upper portion of the polyaxial head; and tightening the set screw to direct the rod to interact with the collet to securely fix an angular orientation of the bone fixation screw with respect to the polyaxial head.

Clause 15—The method of any preceding clause, wherein the collet and polyaxial head are preassembled and attached in unison to the head of the bone fixation screw.

Clause 16—The method of any preceding clause, wherein the collet is installed into the collet cavity from a top and pushed down to compress each flange so that at least one flange passes through at least one relief cut defined within the polyaxial head to retain the collet.

Clause 17—The method of any preceding clause, wherein one or more slits separate the multiple flanges to enable at least a portion of the collet to expand as the head of the bone fixation screw passes through the collet.

Clause 18—The method of any preceding clause, wherein a hinge provides a circumferential connection between a first side and a second side of a body of the collet to enable the first side and the second side to contract or expand about the hinge.

Clause 19—The method of any preceding clause, wherein tightening the set screw creates a wedging action applying downward force to the collet via the rod and compresses the multiple flanges around the head of the bone fixation screw.

Clause 20—A polyaxial spinal fixation system comprising: a polyaxial head having an upper section and a lower section, the upper section having two upstanding members comprising internal threading therein; the lower section having a collet cavity having a first section, a second section, and a third section; wherein the first section includes a collet retention groove, a collet assembly groove, and an upper ledge at a top portion of the collet retention groove; the second section has a partially spherical concave surface and defines a plurality of relief cuts; and the third section has a conical shape terminating in a lip; a bone fixation screw having a head and a threaded shank; a rod configured for insertion into the two upstanding members; a set screw having threads thereon configured to mate with the internal threading of the polyaxial head; and a collet configured for insertion into the collet cavity, wherein the collet further comprises a split-ring cylindrical body having a first side and a second side separated at a first end by a separation and joined at a second end by a hinge, and wherein the collet further comprises an upper portion and a lower portion, the upper portion including one or more tabs extending outwardly from an outer cylindrical surface, and the lower portion including multiple flanges separated by multiple slits, each flange of the multiple flanges having an external surface having a partially spherical convex surface and a conical surface, and an internal surface having at least one partially spherical concave surface, a cylindrical surface, and a conical surface.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.”

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the embodiments are not limited in its application to the details of construction and the arrangement of components set forth in the description or illustrated in the drawings. The invention is capable of other embodiments and of being practiced or of being carried out in various ways. Unless limited otherwise, the terms "connected," "coupled," "in communication with," and "mounted," and variations thereof herein are used broadly and encompass direct and indirect connections, couplings, and mountings. In addition, the terms "connected" and "coupled" and variations thereof are not restricted to physical or mechanical connections or couplings.

The foregoing description of several embodiments of the invention has been presented for purposes of illustration. It is not intended to be exhaustive or to limit the invention to the precise steps and/or forms disclosed, and obviously many modifications and variations are possible in light of the above teaching.

What is claimed is:

1. A polyaxial spinal fixation system comprising:

a polyaxial head having an upper section and a lower section, the upper section having two upstanding members comprising internal threading therein; the lower section having a collet cavity having an upper portion and a lower portion, wherein the upper portion includes a collet retention groove and an upper ledge at a top portion of the collet retention groove; and wherein the lower portion includes a first section, a second section, and a third section; wherein the first section has a partially spherical concave surface; and the second section has a conical surface terminating in a lip;

a bone fixation screw having a head and a threaded shank;

a rod configured for insertion into the two upstanding members;

a set screw having threads thereon configured to mate with the internal threading of the polyaxial head; and a collet configured for insertion into the collet cavity, wherein the collet further comprises a split-ring cylindrical body having a hinge thereon, and wherein the collet further comprises an upper portion and a lower portion, the upper portion including one or more tabs extending outwardly from an outer cylindrical surface, and the lower portion including multiple flanges separated by multiple slits, each flange of the multiple flanges having an external surface having a partially spherical convex surface and a conical surface, and an internal surface having at least one partially spherical concave surface, a cylindrical surface, and a conical surface, wherein the internal surface of at least one flange comprises a first partially spherical concave surface with a first radius and a second partially spherical concave surface with a second radius, wherein the second radius is smaller than the first radius.

2. The polyaxial spinal fixation system of claim 1, wherein the two upstanding members of the upper section define a U-shaped channel.

3. The polyaxial spinal fixation system of claim 2, wherein the rod is secured within the U-shaped channel by the set screw.

4. The polyaxial spinal fixation system of claim 1, wherein the internal threading is tapered or chamfered to facilitate ease of entry of the set screw.

5. The polyaxial spinal fixation system of claim 1, wherein the split-ring cylindrical body further comprises a first side and a second side, wherein the first side and the second side are joined at the hinge.

6. The polyaxial spinal fixation system of claim 1, wherein the slits are arranged parallel to a vertical axis of the split-ring cylindrical body and disposed circumferentially about the split-ring cylindrical body.

7. The polyaxial spinal fixation system of claim 1, wherein one or more of the slits extends beyond the lower portion and into the upper portion of the collet.

8. The polyaxial spinal fixation system of claim 1, further comprising a collet assembly groove comprising a collet assembly groove diameter that is greater than a tab diameter.

9. The polyaxial spinal fixation system of claim 8, wherein the collet retention groove is positioned below the collet assembly groove and the collet retention groove has a collet groove diameter that is greater than the tab diameter.

10. The polyaxial spinal fixation system of claim 9, wherein a collet retention groove diameter is not coaxial with a central axis of the polyaxial head.

11. The polyaxial spinal fixation system of claim 1, wherein the second section has a first diameter adjacent the first section and a second diameter adjacent the lip, wherein the first diameter is larger than the second diameter.

12. The polyaxial spinal fixation system of claim 11, wherein the third section comprises a cylindrical surface having a third section diameter smaller than the second diameter of the second section to define the lip at a junction of the second section and the third section.

13. A method for installing a polyaxial spinal fixation system comprising:

inserting a bone fixation screw using an insertion tool;

installing a collet having a lower portion of the collet having multiple flanges into a collet cavity of a lower section of a polyaxial head from a top by pushing down to compress each flange so that at least one flange passes through at least one relief cut defined within the polyaxial head to retain the collet;

rotating the collet within the collet cavity to position one or more tabs within a collet retention groove but below an upper ledge to limit rotation of the collet within the polyaxial head;

selectively translating the collet within the collet cavity between the upper ledge and a lip;

attaching the collet to the bone fixation screw by contacting the lower portion of the collet with the head of the bone fixation screw such that the multiple flanges splay outwardly to accept the head within the lower portion wherein a first portion of each flange at least partially contacts a lower hemisphere of the head and a second portion of each flange at least partial contacts an upper hemisphere of the head to frictionally hold the head of the bone fixation screw within the collet;

inserting a rod into a U-shaped channel of the polyaxial head;

installing a set screw to engage with an internal threading within an upper portion of the polyaxial head; and tightening the set screw to direct the rod to interact with the collet to securely fix an angular orientation of the bone fixation screw with respect to the polyaxial head.

14. The method of claim 13, wherein the collet and polyaxial head are preassembled and attached in unison to the head of the bone fixation screw.

15. The method of claim 13, wherein one or more slits separate the multiple flanges to enable at least a portion of the collet to expand as the head of the bone fixation screw passes through the collet.

16. The method of claim 13, wherein a hinge provides a circumferential connection between a first side and a second side of a body of the collet to enable the first side and the second side to contract or expand about the hinge.

17. The method of claim 13, wherein tightening the set screw creates a wedging action applying downward force to the collet via the rod and compresses the multiple flanges around the head of the bone fixation screw.

18. A polyaxial spinal fixation system comprising:

a polyaxial head having an upper section and a lower section, the upper section having two upstanding members comprising internal threading therein; the lower section having a collet cavity having an upper portion and a lower portion; wherein upper portion includes a collet retention groove, and wherein the lower portion includes a first section, a second section, and a third section; wherein the first section has a partially spherical concave surface; and the second section has a conical surface terminating in a lip;

a bone fixation screw having a head and a threaded shank;

a rod configured for insertion into the two upstanding members;

a set screw having threads thereon configured to mate with the internal threading of the polyaxial head; and a collet configured for insertion into the collet cavity, wherein the collet further comprises a split-ring cylindrical body having a first side and a second side separated at a first end by a separation and joined at a second end by a hinge, and wherein the collet further comprises an upper portion and a lower portion, the upper portion including one or more tabs extending outwardly from an outer cylindrical surface, and the lower portion including multiple flanges separated by multiple slits, each flange of the multiple flanges having an external surface having a partially spherical convex surface and a conical surface, and an internal surface having at least one partially spherical concave surface, a cylindrical surface, and a conical surface, wherein the internal surface of at least one flange comprises a first partially spherical concave surface with a first radius and a second partially spherical concave surface with a second radius, wherein the second radius is smaller than the first radius.

* * * * *